United States Patent
Wooley et al.

(10) Patent No.: US 10,329,381 B2
(45) Date of Patent: Jun. 25, 2019

(54) DEGRADABLE POLYCARBONATE SPORT FISHING MATERIALS

(71) Applicant: THE TEXAS A&M UNIVERSITY SYSTEM, College Station, TX (US)

(72) Inventors: Karen L. Wooley, College Station, TX (US); Simcha E. Felder, College Station, TX (US); Brooke A. Versaw, College Station, TX (US); Ashlee A. Jahnke, College Station, TX (US); Lauren A. Link, Tempe, AZ (US); Mark W. Wooley, College Station, TX (US); Charles A. Hinton, College Station, TX (US); William R. Howell, Jr., College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/650,244

(22) Filed: Jul. 14, 2017

(65) Prior Publication Data
US 2018/0016390 A1 Jan. 18, 2018

Related U.S. Application Data

(60) Provisional application No. 62/362,885, filed on Jul. 15, 2016.

(51) Int. Cl.
*C08G 63/02* (2006.01)
*C08G 64/02* (2006.01)
*C08G 75/045* (2016.01)
*C12P 19/04* (2006.01)
*C08G 75/02* (2016.01)
*C08G 75/12* (2016.01)

(52) U.S. Cl.
CPC ......... *C08G 64/0216* (2013.01); *C08G 75/02* (2013.01); *C08G 75/045* (2013.01); *C08G 75/12* (2013.01); *C12P 19/04* (2013.01)

(58) Field of Classification Search
USPC ....................................................... 528/201
See application file for complete search history.

(56) References Cited

U.S. PATENT DOCUMENTS

2012/0184682 A1   7/2012  Dasgupta

FOREIGN PATENT DOCUMENTS

WO   2012/051448   4/2012

OTHER PUBLICATIONS

International Search Report and Written Opinion for PCT Patent Application No. PCT/US2017/042061, dated Oct. 9, 2017; 15 pages.
Link, Lauren A., et al. "Photo-cross-linked Poly (thioether-co-carbonate) Networks Derived from the Natural Product Quinic Acid." ACS applied materials & interfaces 6.20 (2014): 17370-17375; 6 pages.

*Primary Examiner* — Terressa Boykin
(74) *Attorney, Agent, or Firm* — Baker Botts L.L.P.

(57) ABSTRACT

Degradable polycarbonates network based bulk materials are provided. The bulk materials of the present disclosure may be produced having a wide range of tunable mechanical, physical, and thermal properties and are hydrolytically degradable. The bulk materials of the present disclosure may be suitable for the manufacture of a variety of sport fishing equipment or other equipment for water use or that may benefit from hydrolytic degradation in the environment.

23 Claims, 4 Drawing Sheets

DEGRADABLE POLYCARBONATE SPORT FISHING MATERIALS

PRIORITY CLAIM

This application claims priority under 35 U.S.C. § 119 to U.S. Provisional Patent Application Ser. No. 62/362,885, filed Jul. 15, 2016, titled "Degradable Polycarbonate Sport Fishing Materials," which is incorporated by reference herein in its entirety.

STATEMENT OF GOVERNMENT INTEREST

This invention was made with government support under Grant Nos. CHE-1057441 and CHE-1410272 awarded by the National Science Foundation. The government has certain rights in the invention.

BACKGROUND

Over the past few decades, there has been a significant interest in the preparation of polymers that originate from renewable resources, typically based upon carbohydrates or fatty acids, in order to diminish the dependence on petroleum products, and that can also undergo degradation, to reduce landfill accumulation of waste. Polycarbonates, especially those based upon bisphenol A, are a foundation material for engineering applications. Many of these polycarbonates, however, form bioresorbable degradation products that are toxic and/or carcinogenic. Degradable polymers also find use in biomedicine (e.g., sutures, orthopedic devices, tissue engineering, drug delivery devices, etc.), where incorporation of biocompatibility and biodegradability is important. For this purpose, the polymers used are typically of esters, which undergo hydrolysis to afford products containing carboxylic acid and alcohol groups, or carbonates, especially aliphatic carbonates that undergo hydrolytic degradation to give carbon dioxide and alcohols.

Recent demand for sustainable commodity plastics has prompted interest in the development of new classes of naturally-derived polymers. Naturally-derived polymers can be in the form of polymers that are isolated from nature, e.g. polysaccharides, polynucleic acids, polypeptides, etc. or may be produced by polymerization processes conducted upon naturally-derived monomers. Natural products are molecules that can be isolated from natural sources, such as fungi, bacteria, plants, or animals, etc. These molecules include sugars, amino acids, neolignans, cyclitols, flavinoids, and many others. An attractive characteristic of both natural and synthetic polymers derived from renewable feedstocks is that they can be degraded by photochemical, thermal, or hydrolytic means, to regenerate the natural precursors.

In the sports fishing industry, a wide array of equipment and accessories are created using a variety of synthetic materials. Discarded and lost fishing tackle causes pollution, kills wildlife, and endangers humans in bodies of water around the world. For instance, it has been previously found that wild fish regularly eat soft plastic lures that litter their environment, which can lead to death by clogging the digestive system of the fish. Many commercial soft plastic lures also can leach dangerous chemicals, such as phthalates, over time. These issues are magnified significantly when considered on a global scale; some estimate that as much as 20 million pounds of lure material are lost each year.

SUMMARY

The present disclosure provides a hydrolytically-degradable device including a hydrolytically-degradable polycarbonate network that includes a polyhydroxyl monomer that is a natural product, such a polyhydroxyl monomer modified to consume at least one hydroxyl group with an allyl carbonate group, or any mixtures thereof; a crosslinking comonomer; and a functional additive.

The present disclosure also provides a hydrolytically-degradable device including a bulk material that includes a polyhydroxyl monomer that is a natural product, such a polyhydroxyl monomer modified to consume at least one hydroxyl group with an allyl carbonate group, or any mixtures thereof; a crosslinking comonomer; and a functional additive.

According to further embodiments, which may be combined with either the hydrolytically-degradable device above or with one another or any other embodiments disclosed herein unless clearly mutually exclusive, i) the polyhydroxyl monomer may be a molecule including two or more hydroxyl groups; ii) the polyhydroxyl monomer modified to consume at least one hydroxyl group with an allyl carbonate group may include an allyl glucopyranoside monomer; iii) the polyhydroxyl monomer modified to consume at least one hydroxyl group with an allyl carbonate group may include an allyl sucrose monomer; iv) the crosslinking comonomer may be a thiol comonomer; v) the polycarbonate network or bulk material may have a glass transition temperature in the range of from −25° C. to 175° C.; vi) the polycarbonate network or bulk material may have a storage modulus in the range of from 0.1 MPa to 4000 MPa; vii) the functional additive may be selected from the group consisting of glitters, dyes, fragrances, flavorants, insect repellents, photoacid generators, pH sensitive moieties, plasticizers, tougheners, and any combination thereof; viii) the polycarbonate network or bulk material may be a film or pellet; ix) the polycarbonate network or bulk material may be located in a fishing lure, fishing rod, fishing line or wire, hook, net, bobber, other tackle, or clothing.

The disclosure also provides a method, which may be used alone or in combination with any of the embodiments disclosed above or otherwise herein unless clearly mutually exclusive. The method includes providing a plurality of polyhydroxyl monomers that are natural products, a plurality of such polyhydroxyl monomers modified to consume at least one hydroxyl group with an allyl carbonate group, or any mixtures thereof, a plurality of crosslinking monomers, and a functional additive; mixing the polyhydroxyl monomers, the plurality of crosslinking monomers, and the functional additive to form a resin; curing the resin to form a bulk material; and making a hydrolytically-degradable device that encounters an aqueous environment and degrades a set time thereafter.

According to further embodiments, which may be combined with either hydrolytically-degradable device above or with one another or any other embodiments disclosed herein unless clearly mutually exclusive, i) curing the resin to form a bulk material may include irradiating the resin using UV light; ii) curing the resin to form a bulk material may include heating the resin; iii) the method may include controlling at least one mechanical or physical property of the bulk material; iv) the at least one mechanical or physical property may include a glass transition temperature value or a storage modulus value.

The present specification discloses a number of polyhydroxyl monomers in the Figures, Description, and Examples. Each of these polyhydroxyl monomers may be used alone or in combination with any other polyhydroxyl monomer.

The present specification discloses a number of crosslinking comonomers, particularly thiols in the Figures, Description, and Examples. Each of these crosslinking comonomers, particularly thiols, may be used alone or in combination with any other crosslinking comonomer, particularly a thiol.

BRIEF DESCRIPTION OF THE DRAWINGS

A more complete understanding of the present disclosure and advantages thereof may be acquired by referring to the following description taken in conjunction with the accompanying drawings, which relate to the present disclosure.

DESCRIPTION

Figure 1:
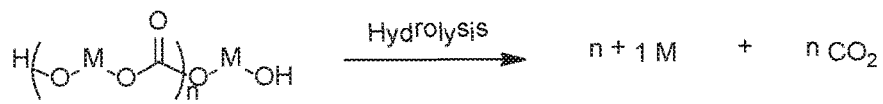
FIG. 1 is a reaction scheme for hydrolysis of the polycarbonates.

The present disclosure provides hydrolytically-degradable bulk materials for use in hydrolytically-degradable devices. The hydrolytically-degradable devices may be sports fishing equipment or any other type of equipment or device that preferably may degrade when exposed to water. The bulk materials of the present disclosure include, but are not limited to, films and pellets. The bulk materials of the present disclosure may be used in the manufacture of fishing lures, fishing rods, fishing line or wire, hooks, nets, bobbers, other tackle, and clothing. The bulk materials may include other equipment intended for water use or that may benefit from hydrolytic degradation in the environment The bulk materials of the present disclosure may generally include polycarbonate networks. Such polycarbonate networks are hydrolytically labile and may release a polyhydroxyl monomer and carbon dioxide upon degradation. The polycarbonate networks of the present disclosure may benefit from useful physical properties, such as improved and/or useful mechanical and/or thermal properties. These polycarbonate networks may be tuned to have specific physical, mechanical, and degradation profiles based on the choice of the natural product-based monomer(s), crosslinker(s), and functional additive(s) used in their production.

The polycarbonates and polycarbonate networks used to form the bulk materials of the present disclosure are described generally in International Patent Application No. PCT/US2011/056204, the entire disclosure of which is incorporated herein by reference.

In general, such polycarbonate networks include two or more polycarbonates associated into a polymer network. The polycarbonate network may be an interpenetrating polymer network or semi-interpenetrating polymer network. A crosslinked polycarbonate network may be formed by providing one or more linear polycarbonates followed by forming one or more crosslinks between another linear polycarbonate. A crosslinked polycarbonate network may also be formed by direct crosslinking of multifunctional comonomers. The crosslinks may be formed using any technique. For example, the crosslinks may be formed using chemical routes. The crosslinks also may be formed using photo-initiated reactions (e.g., thiol-ene reactions) on functionalized polymers and/or monomers.

As used herein, the term "polyhydroxyl monomer" refers to any molecule having two or more hydroxyl groups and may be monomeric or polymeric. In general, suitable polyhydroxyl monomers for use in the present disclosure are those polyhydroxyl monomers that are capable of reacting with a carbonylation agent or other comonomers to form a polycarbonate. A suitable polyhydroxyl monomer may be a natural product (i.e. derived wholly or in part from a biological synthesis pathway performed by a living organism). By using polyhydroxyl monomers that are natural products, the resulting polycarbonates will, among other things, be less dependent on petrochemicals, have tunable mechanical properties for multiple types of applications, and undergo degradation (e.g., hydrolysis) to release those natural products. Examples of suitable polyhydroxyl monomers that are natural products, include, but are not limited to, saccharides such as, for example, glucose (e.g., D-glucose), mannose, fructose, sucrose, trehalose, lactose, raffinose, stachylose, and the like; polyphenolic molecules such as, for example, quercetin, magnolol, honokiol, catechin, epicatechin, epicatechin 3-gallate, epigallocatechin, epigallocatechin 3-gallate, tannin, teaflavins, and other such flavonoids, and other polyphenolic natural products that derive from teas and other sources; derivatives of polyphenolic molecules such as, for example quinic acid (derived from chlorogenic acid), and combinations thereof.

A polyhydroxyl monomer may be modified to consume at least one hydroxyl group with an allyl carbonate group. The polyhydroxyl monomer thus modified may be described as functionalized.

The polycarbonates of the present disclosure may include more than one type of polyhydroxyl monomer.

In general, the polycarbonates used to form the polycarbonate networks of the present disclosure include two or more polyhydroxyl monomer repeating units that may be linked by a carbonate moiety. The polycarbonates also may include networks of more than one polycarbonate molecule (e.g., crosslinked polycarbonate networks), as well as crosslinks between polycarbonate molecules.

The polycarbonates used to form the polycarbonate networks of the present disclosure may be represented by the formula:

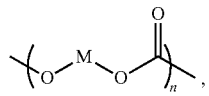

wherein O-M-O represents a polyhydroxyl monomer and n is >1. Hydrolysis of the polycarbonates of the present disclosure may be represented by the reaction scheme of FIG. 1.

The bulk materials of the present disclosure may be prepared by mixing a functionalized polyhydroxyl monomer with a suitable crosslinking comonomer or comonomers to form a homogeneous resin. The homogeneous resin may then be deposited into a mold, such as a clear mold and cured to produce crosslinked polycarbonate networks. The curing may be performed using a photo-initiated reaction, including, but not limited to, a thiol-ene reaction. A radical initiator may be added to the homogeneous resin to facilitate this photo-initiated reaction. Curing may be performed by irradiating the homogeneous resin with UV light. A clear mold is typically used in conjunction with a photo-initiated curing reaction. Curing may also be performed by heating the homogeneous resin. Different types of curing may be used simultaneously or sequentially. As would be understood by a person of ordinary skill in the art having the benefit of the present disclosure, the rapid and efficient curing of the bulk materials makes them suitable for products having a wide variety of shapes and structures.

The polycarbonate networks of the present disclosure may be tailored to have a broad range of physical and mechanical properties. Tuning of these properties may be performed by varying the crosslinking conditions. For example, the properties may be tuned by varying the average number of functional groups of the functionalized polyhydroxyl monomer (also referred to as average functionality). The properties may also be tuned by varying the crosslinking comonomers used to form the homogeneous resin. The properties may also be tuned by varying the speed and temperature of the photo-initiated crosslinking reaction or the heating reaction. To further tune the properties of the polycarbonate networks, a range of functional additives may be introduced into the resins prior to crosslinking to produce composite materials with various mechanical, physical, and aesthetic properties. Alternatively, these additives may be introduced after the crosslinking has been performed. Possible functional additives include, but are not limited to, glitters, dyes, fragrances, flavorants, insect repellents, photoacid generators, pH sensitive moieties, plasticizers, tougheners, and combinations thereof. The polycarbonate networks of the present disclosure may be tuned to have desirable thermal degradation temperature values ("$T_d$") in the range of from 200° C.-325° C., particularly 260° C.-325° C. The polycarbonate networks of the present disclosure may be tuned to have glass transition temperature values ("$T_g$") in the range of from −25° C. to 175° C. Polycarbonate networks used in soft devices, such as lures, may have a $T_g$ value between −25° C. and 75° C., between 0° C. and 50° C., or between −25° C. and 20° C. Polycarbonate networks used in rigid devices, such as hooks and rods, may have a $T_g$ value higher than that expected to be normally encountered in the environment during use. For instance, they may have a $T_g$ of between 20° C. and 175° C., between 40° C. and 175° C., or between 50° C. and 175° C.

The polycarbonate networks of the present disclosure may also be tuned to have storage moduli values ("E'") in the range of from 0.1 MPa to 4000 MPa. Storage moduli values may also be in the range of from 0.1 MPa to 2600 MPa, or in the range of from 0.2 MPa to 35 MPa. These, and other, properties may be tuned to match the properties of existing commercially available sport fishing gear. Examples of thermal and mechanical properties of commercially available fishing equipment are provided in Table 1 below.

TABLE 1

Thermal Transitions and Moduli Exhibited by Commercially Available Soft Plastic Lures

| Commercial Bait | $T_g$ (° C.) | $T_d$ (° C.) | E' at 5° C. (MPa) | E' at 25° C. (MPa) |
|---|---|---|---|---|
| Warcraft Soft Bait 1 | −6 | 271 | 0.28 | 0.27 |
| Warcraft Soft Bait 2 | — | 268 | 0.31 | 0.31 |
| Tioga Minnow | — | 234 | 0.09 | 0.09 |
| Strike King Shad | −8 | 276 | 0.32 | 0.31 |
| Berkley PowerBait Worm | −11 | 274 | 2.21 | 2.20 |
| Berkley Gulp! Minnow | — | 288* | 0.26 | 0.25 |
| Berkley Gulp! Shad | — | 301** | 0.57 | 0.51 |

*Significant mass loss observed over 60-240° C.
**Significant mass loss observed over 40-280° C.

The polycarbonate networks of the present disclosure may have good resistance to degradation in the environment for a period of time for their utilization, yet undergo degradation when remaining for prolonged periods of time (weeks to months). This degradation may be measured in at least two ways.

First, the polycarbonate networks may be resistant to thermal degradation until a particular temperature is reached. Resistance to thermal degradation may be quantified by thermogravimetric analysis of the onset, $(T_d)_{onset}$, which may be at least 284° C. or at least 290° C., or between 284° C. and 302° C., or between 290° C. and 302° C.

Second, polycarbonate networks may be resistant to hydrolytic degradation for weeks to months under typical environmental conditions, and then undergo breakdown to the polyhydroxyl natural product, carbon dioxide and other byproducts at a later time or when ingested. Hydrolytic degradation may be quantified by immersing the polycarbonate network in water at a set temperature, pH and ionic strength for a set period of time, then observing either a degradation product or a degradation-related property of the polycarbonate network. For uses, such as fishing and water-relating products, where the polycarbonate network needs to degrade in the environment, the hydrolytic degradation test conditions may be designed to mimic the environment and a product may be deemed to be undergoing degradation when a condition linked to rendering it no longer environmentally harmful is achieved.

For instance, conditions may involve pH values below or above neutrality (e.g. that of digestive systems or seawater, respectively), or the water temperature may mimic use conditions, such as freeze-thaw cycles or average water temperature, such as 20° C. or 25° C. The water may be fresh or salt water depending on typical use conditions. The number of days under which the test is performed may balance product life and rapid degradation when lost in the environment.

Tests in which harsher conditions, such as temperatures above 50° C. or salinity at least 5× that of average seawater, are used to accelerate testing are also possible, so long as the results can be correlated with actual expected behaviour in the environment.

Test conditions may include other, more specialized features, such as exposure to UV light to mimic sun damage, wetting and drying cycles, or movement to mimic wave action.

Degradation may be measured, in some examples, by detectable and statistically significant over control sample amounts of polyhydroxyl monomer or another product of hydrolysis of the polycarbonate network.

Degradation may also be measured by a change in a mechanical property, such as a change drop in the storage modulus below a threshold, or by a simpler measure, such as the inability of the polycarbonate network to hold its physical form when picked up.

In some examples where even small amounts of the polycarbonate network remaining intact are problematic, degradation may not be deemed to have occurred until at least 90% of the polycarbonate network has dissolved in the water.

Polycarbonate networks may be degraded using the poly (thioether-co-carbonate) network degradation system described in the Examples with suitable variations according to the principles described above.

EXAMPLES

To facilitate a better understanding of the present invention, the following examples of certain aspects are given. In no way should the following examples be read to limit, or define, the entire scope of the invention.

Example 1

Glucopyranoside Monomer Networks

Allyl glucopyranoside monomer mixtures may be prepared by the reaction of a glucopyranoside with allyl chloroformate in the presence of tetramethylethylenediamine, or another suitable base. The glucopyranoside monomers were then isolated from the reaction mixture to form the allyl glucopyranoside monomer mixture. The allyl glucopyranoside monomer mixture may contain glucopyranoside monomers of varying levels of functionality conferred by the allyl group. The allyl glycopyranoside monomers in the mixture may be described, however, as having an average allyl functionality.

The composition of the allyl glucopyranoside monomer mixture may be tuned to a different average functionality by varying the equivalents of allyl chloroformate added to the starting glucopyranoside. For example, adding 3.5 equivalents of allyl chloroformate yielded an allyl glucopyranoside monomer mixture with an average functionality of 2.5 while adding 6.1 equivalents yielded an allyl glucopyranoside monomer mixture with an average functionality of 3.6. These allyl glucopyranoside monomer mixtures may be purified by column chromatography, with a gradient eluent of ethyl acetate and hexane, to yield separated allyl glucopyranoside monomers with two, three, and four allyl functionalities.

Allyl glucopyranoside monomers can be crosslinked using any suitable thiol comonomer, including but not limited to, 1,2-ethane dithiol, 2,3-butanedithiol, 1,6-hexanedithiol, trimethylolpropanyl tris(3-mercaptopropionate), tetraethylene glycol bis(3-mercaptoproprionate), 1,4-butane diol bismercaptoacetate, asparagusic acid, lipoic acid, and lipoamide, and combinations thereof. In a general procedure, allyl glucopyranoside monomers are mixed with multifunctional thiol comonomers, based on a molar equivalence of functional groups (alkene to thiol) to produce homogeneous resins. A radical initiator (1-10 wt %), is then added to the resin, which can be cast into a mold to form various geometries. Radical initiators can include, but are not limited to, 2,2-dimethoxy-2-phenylacetophenone, 2,2'-azobis(2-methylpropionitrile), potassium persulfate, benzoyl peroxide, 4,4'-azobis(4-cyanovaleric acid), and combinations thereof. Polymerization via crosslinking thiol comonomers may be initiated through exposure to UV irradiation, heat, or both to produce uniform bulk materials. These materials may then be postcured at 120° C. for at least 4 h to vulcanize any remaining thiol groups.

The properties of the bulk materials can be modulated and fine-tuned by varying the crosslinking conditions. For example, the average number of allyl functionalities on the allyl glucopyranoside monomer, as well as the length and rigidity of the thiol comonomer or comonomers, affect the crosslink density of the final material. The number of equivalents of thiol used compared to alkene also affects the crosslink density of the bulk material. By varying these three factors, and others, materials with a range of moduli and degradation profiles can be generated.

Figure 2:
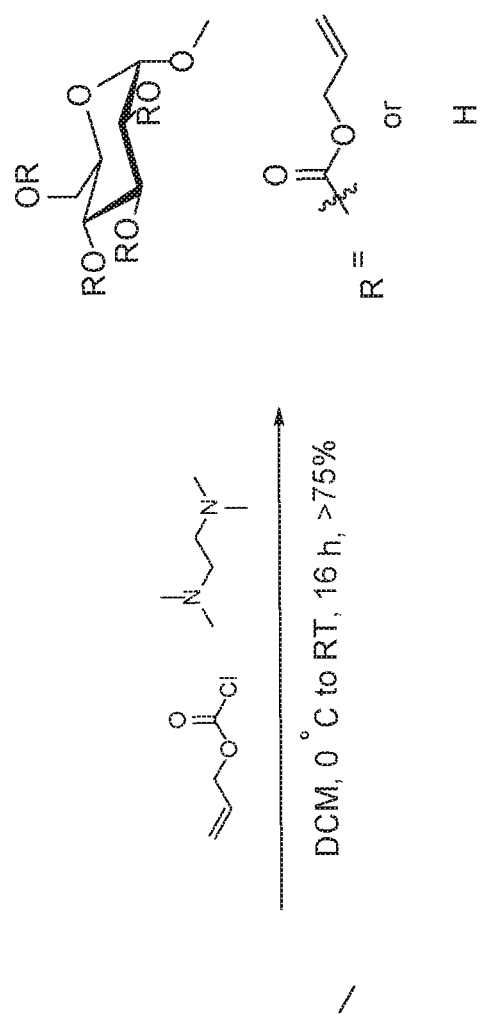
FIG. 2 is a reaction scheme for preparing allyl glucopyranosides.

Ally glucopyranoside monomer mixtures were prepared according to the reaction scheme shown in FIG. 2. A solution of methyl glucopyranoside (6.0010 g, 30.9 mmol) and tetramethylethylenediamine (21.0 mL, 140 mmol) in anhydrous dichloromethane ("DCM") (40 mL) was cooled to 0° C. Allyl chloroformate (20.0 mL, 188 mmol), in 13 mL of anhydrous DCM, was added slowly to the glucopyranoside solution over several minutes. The reaction was allowed to warm to room temperature over 16 hours. The reaction mixture was then filtered to remove any precipitates, the filtrate was diluted with additional DCM and was washed with a saturated sodium bicarbonate, 5% HCl aqueous solution, and deionized water. The organic layer was then dried with sodium sulfate, and concentrated to yield a mixture of differently functionalized allyl glucopyranoside monomers (13.66 g, 3.6 average allyl groups per glucopyranoside).

Figure 3:
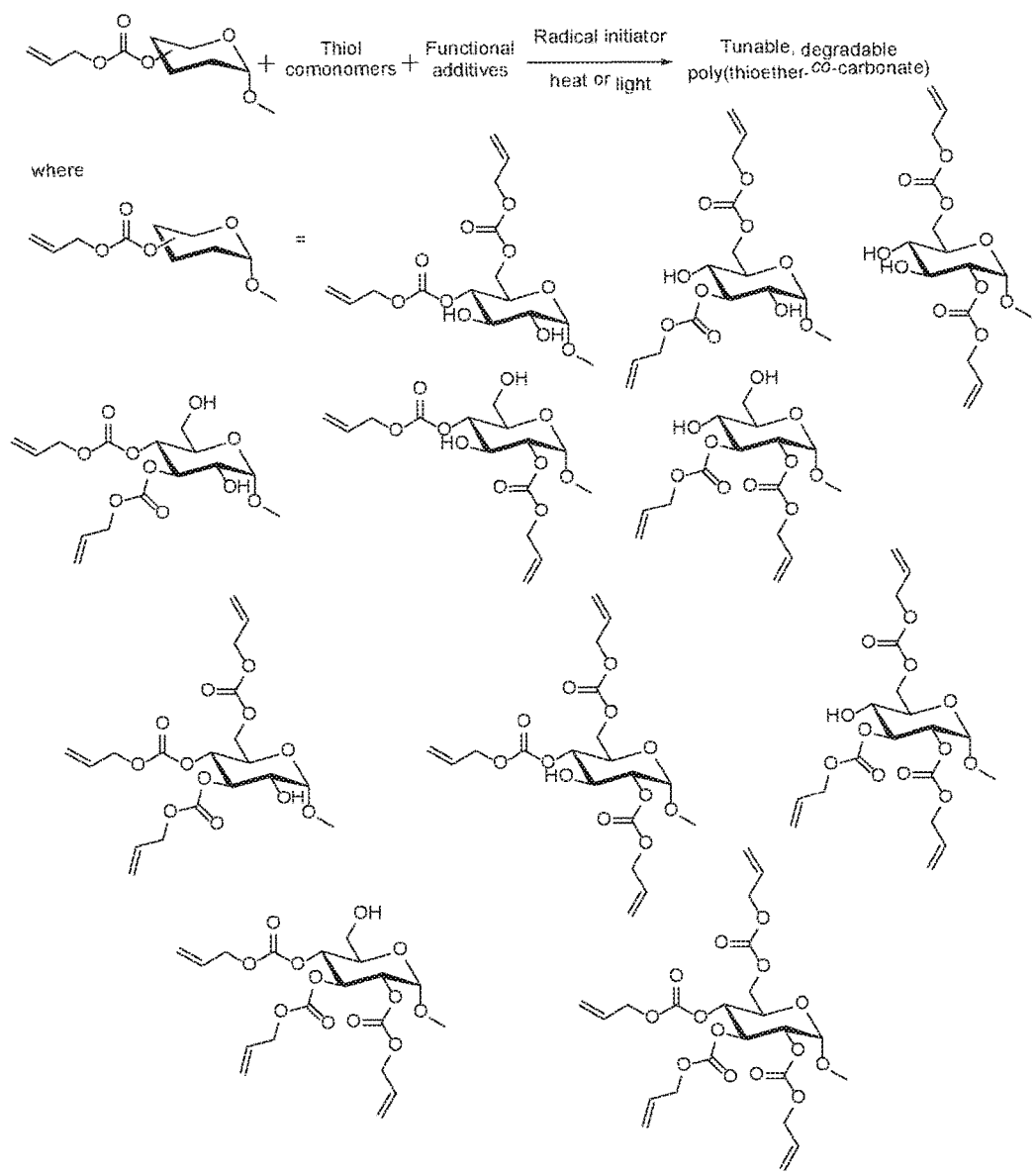
FIG. 3 is a reaction scheme for crosslinking allyl glucopyranoside monomers with thiol comonomers.

The allyl glucopyranoside monomers were then crosslinked with thiol comonomers according to the general reaction scheme shown in FIG. 3. In a vial, allyl glucopyranoside monomers and the desired thiol (1:1 alkene:thiol) were mixed by sonication/vortexing until a homogeneous mixture was achieved, any desired additives can be incorporated at reaction step. The radical initiator, 2,2-dimethoxy-2-phenylacetophenone (1 wt %), was added and mixed into the resin by sonication/vortexing. The resins were loaded into two molds, one pellet and one thin film, and exposed to UV light (365 nm) for 1 minute per side. The materials were post-cured in the vacuum oven at 120° C. overnight to remove any remaining thiols.

Figure 5:
FIG. 5 is a reaction scheme for thiol preparation.
Figure 4:
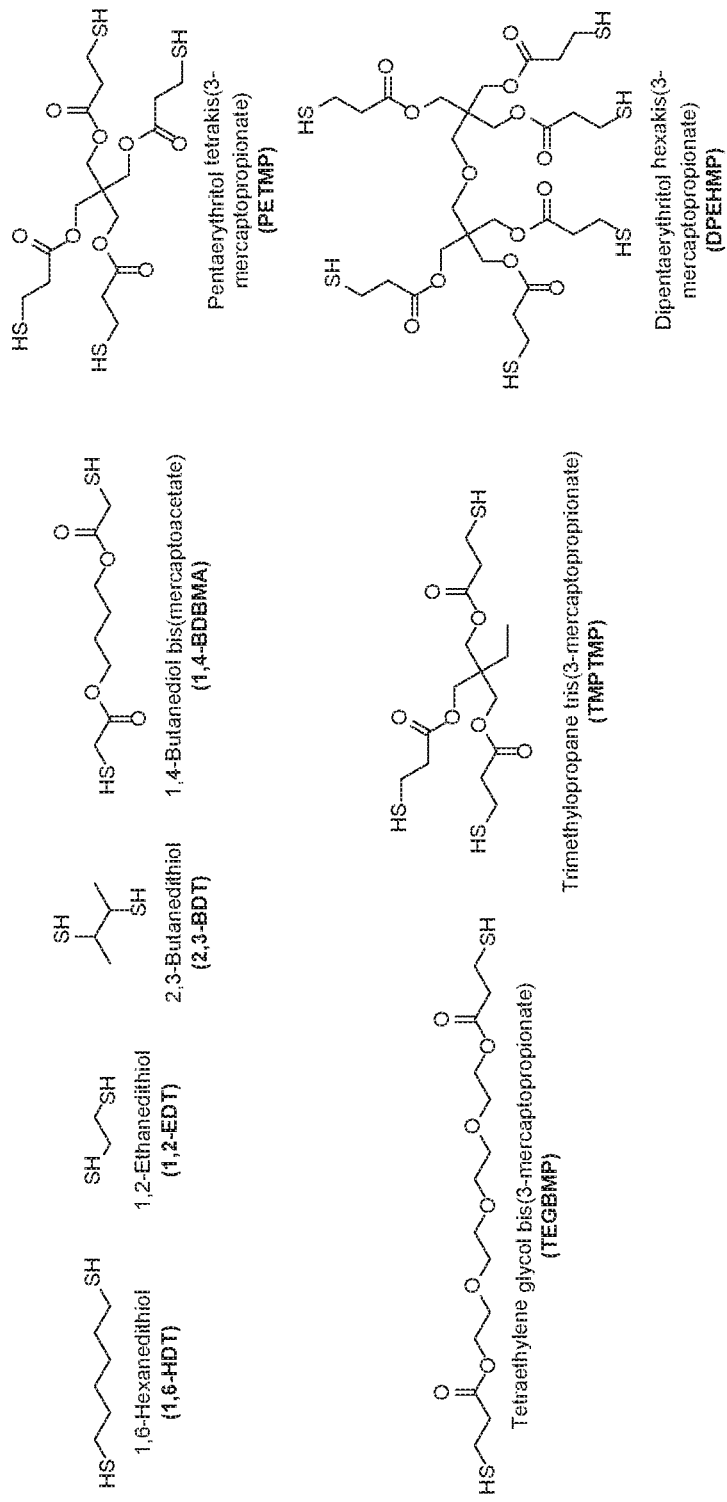
FIG. 4 is a set of structural formulas of multifunctional thiols.

Eight separate poly(thioether-co-carbonate) networks were generated using each of the multifunctional thiols shown in FIG. 4. A thiol based on glycerol as described in Chinese Patent Application 102603583, filed Jul. 25, 2012 (the composition and methods of which are incorporated by reference herein) or prepared according to the scheme of FIG. 5 may also be used. In addition, a thiol based on glycerol and cysteine prepared according to the scheme of FIG. 6 may also be used.

The thermal and mechanical properties of the resulting poly(thioether-co-carbonate) networks were characterized and the results are summarized in Table 2. Glass transition temperatures were measured using differential scanning calorimetry ("DSC") by a Mettler-Toledo DSC822 (commercially available from Mettler-Toledo, Columbus, Ohio) with a heating rate of 10° C./min. The $T_g$ was taken as the midpoint of the inflection tangent upon the third heating cycle. Moduli values were measured on a TT-DMA dynamic mechanical analyser from Triton Laboratories with a heating rate of 3° C./min. Low allyl glucose monomers are allyl glucopyranoside monomer mixtures have an average allyl functionality of 2.5. High allyl glucose monomers are allyl glucopyranoside monomer mixtures have an average allyl functionality of 3.6.

TABLE 2

Thermal Transition Data and Moduli Exhibited by Thiol-Glusopyranoside Networks.

| Crosslinker | Number of Thiols | Glucose Monomer | $T_{d,\ onset}$ (° C.) | $T_g$ (° C.) | E' at 5° C. (MPa) | E' at 25° C. (MPa) |
|---|---|---|---|---|---|---|
| 1,6-HDT | 2 | Low allyl | 310 | — | — | — |
| | | High allyl | 318 | 29 | 20.2 ± 1.6 | 19.1 ± 1.0 |
| 1,2-EDT | 2 | Low allyl | 287 | 35 | 25.8 ± 1.5 | 24.1 ± 2.0 |
| | | High allyl | 295 | 45 | 17.4 ± 2.7 | 17.1 ± 2.7 |
| 2,3-BDT | 2 | Low allyl | 290 | 29 | 32.2 ± 4.0 | 30.8 ± 3.8 |
| | | High allyl | 298 | 32 | 19.4 ± 0.97 | 17.6 ± 0.57 |
| TEGBMP | 2 | Low allyl | 304 | −11 | 2.84 ± 2.5 | 0.482 ± 0.0069 |
| | | High allyl | 320 | −17 | 1.17 ± 1.1 | 0.387 ± 0.0019 |
| 1,4-BDBMA | 2 | Low allyl | 315 | 2 | 21.6 ± 12.7 | 5.44 ± 4.32 |
| | | High allyl | 325 | 1 | 37.85 ± 1.6 | 2.87 ± 1.4 |
| TMPTMP | 3 | Low allyl | 310 | 35 | 28.0 ± 6.3 | 26.4 ± 6.0 |
| | | High allyl | 312 | 32 | 24.2 ± 9.4 | 23.4 ± 8.4 |
| PETMP | 4 | Low allyl | 301 | 51 | 15.0 ± 1.0 | 14.8 ± 1.0 |
| | | High allyl | 313 | 51 | 18.8 ± 2.4 | 18.3 ± 2.3 |
| DPEHMP | 6 | Low allyl | 279 | 33 | 13.9 ± 1.1 | 13.6 ± 1.2 |
| | | High allyl | 309 | 58 | 13.2 ± 1.5 | 11.5 ± 0.87 |

To further investigate the poly(thioether-co-carbonate) networks, two systems were chosen to probe the effects of functional additives: 1,2-EDT as an example of high $T_g$ material, and TEGBMP as an example of a low $T_g$ material. Commercially available glitter, scent, and dye designed for use in homemade fishing lures (commercially available from Netcraft) were used as additives. The general procedure for photo-cross-linking of poly(thioether-co-carbonate) networks with functional additives was very similar to the procedure used without additives. In a vial, allyl glucopyranoside monomer, thiol (1:1 alkene:thiol), radical initiator (1 wt %), and additive were mixed by sonication/vortexing until a homogeneous mixture was achieved. The resins were loaded into a pellet mold and exposed to UV light (365 nm). The materials were post-cured in the vacuum oven at 120° C. overnight to remove any remaining thiols. The thermal and mechanical properties of the resulting poly(thioether-co-carbonate) networks were characterized and the results are summarized in Table 3.

TABLE 3

Thermal Transition Data and Moduli Exhibited by Thiol-Glucopyranoside Networks with Functional Additives.

| System | Additive | $T_{d,\ onset}$ (° C.) | $T_g$ (° C.) | E' at 5° C.* (MPa) | E' at 25° C. (MPa) |
|---|---|---|---|---|---|
| Low allyl-co-1,2-EDT | None | 286 | 41 | 12.0 ± 0.25 | 11.7 ± 0.34 |
| | Dye | 284 | 36 | 16.2 ± 0.96 | 15.6 ± 0.67 |
| | Scent | 285 | 35 | 7.14 ± 0.31 | 7.10 ± 0.048 |
| | Glitter | 287 | 37 | — | — |
| | All Three | 288 | 34 | 17.5 ± 0.84 | 16.4 ± 0.65 |
| Low allyl-co-TEGBMP | None | 309 | −12 | 1.41 ± 1.4 | 0.307 ± 0.025 |
| | Dye | 307 | −13 | 1.68 ± 1.4 | 0.331 ± 0.021 |
| | Scent | 320 | −13 | 1.63 ± 1.4 | 0.372 ± 0.010 |
| | Glitter | 324 | −10 | 2.46 ± 2.4 | 0.243 ± 0.011 |
| | All Three | 321 | −15 | 1.83 ± 1.7 | 0.320 ± 0.020 |

*Modulus values at 5° C. for low allyl-co-TEGBMP varied widely based on starting temperature of the measurements, resulting in the large observed error.

In order to investigate batch-to-batch variation, a new batch of low allyl glucopyranoside monomer mixture was prepared. The resulting monomer mixture had an average allyl functionality of 2.4. For comparison of properties, samples were prepared, as previously described, using TEGBMP as the thiol. Some batch-to-batch variation based on average allyl functionality of the glucopyranoside monomer mixture was observed. The thermal and mechanical properties of the resulting poly(thioether-co-carbonate) networks were characterized and the results are summarized in Table 4.

TABLE 4

Thermal Transition Data and Moduli Exhibited by the Low Allyl-co-TEGBMP System with Glucopyranoside Monomers from Different Batches.

| Monomer | $T_{d,\ onset}$ (° C.) | $T_g$ (° C.) | E' at 5° C.* (MPa) | E' at 25° C. (MPa) |
|---|---|---|---|---|
| 2.5 avg. functionality | 309 | −12 | 1.41 ± 1.4 | 0.307 ± 0.025 |
| 2.4 avg. functionality | 300 | −21 | 0.868 ± 0.65 | 0.208 ± 0.004 |

*Modulus values at 5° C. for low allyl-co-TEGBMP varied widely based on starting temperature of the measurements, resulting in the large observed error.

Hydrolytic degradation properties of the poly(thioether-co-carbonate) networks may also be investigated. These networks may degrade back to the constituent components. To monitor hydrolytic degradation, discs of the material may be prepared and have their initial mass recorded. The discs may then be submerged in 4 mL of phosphate buffered saline (PBS) at pH 7.4, and placed on a shaker in an incubator, for example at 60 rpm and 37° C. The PBS may be changed weekly. Sample discs may be removed each week and then rinsed with deionized water. One or a few discs may be retained, while the remainder are returned to the fresh PBS in the degradation environment. The total test time may last 25 weeks.

Each retained disc, and the remaining discs upon completion of the test, may be measured to assess any swelling and to assess any mass loss. Swelling and mass loss are indicators of hydrolytic degradation.

A readily hydrolytically degradable poly(thioether-co-carbonate) network may swell to double its original weight within five weeks, followed by rapid mass loss over the next five weeks due to bulk erosion.

Visible physical changes to the discs may also be assessed. Readily hydrolytically degradable poly(thioether-co-carbonate) networks may swell so much they show surface ruptures, exposing the interior of the disc, which may be jelly-like.

In contrast, a poly(thioether-co-carbonate) network that is not readily hydrolytically degradable or hydrophilic may not exhibit substantial swelling, changes to disc shape, or noticeable ruptures. Such a network may degrade primarily by surface erosion and may take at least 20 weeks to show substantial mass loss.

In addition, the compressive modulus of the discs may be assessed above and below the $T_g$ for the particular poly(thioether-co-carbonate) network. Hydrolytic degradation may be deemed to have occurred when the compressive modulus below the $T_g$ has decreased or when the compressive modulus as plotted against temperature no longer shows a sharp drop at the $T_g$ for the particular poly(thioether-co-carbonate) network.

Furthermore, the PBS or the discs may be subject to qualitative or quantitative chemical analysis to detect the presence of the component monomers or the poly(thioether-co-carbonate) network.

Glucopyranoside monomer networks may also be applied using methods similar to those described for sucrose monomer networks below.

Example 2

Sucrose Monomer Networks

Allyl sucrose carbonate monomer mixtures may be prepared using methods similar to those for allyl glucopyranoside monomer networks described above and as further described below.

Allyl sucrose carbonate monomer mixtures may be prepared by the reaction of sucrose with allyl chloroformate in the presence of sodium hydroxide, or another suitable base. The sucrose monomers may be then isolated from the reaction mixture to form the allyl sucrose carbonate monomer mixture. The allyl sucrose carbonate monomer mixture may contain sucrose monomers of varying levels of functionality conferred by the allyl group. The sucrose monomers in the mixture may be described, however, as having an average allyl functionality.

The allyl sucrose carbonate monomer mixture may be tuned to a different average allyl functionality by varying the equivalents of allyl chloroformate added to the sucrose, reaction time, and isolation method.

Sucrose monomers in the allyl sucrose carbonate may be crosslinked using any suitable thiol, including but not limited to 1,2-ethane dithiol, 2,3-butanedithiol, 1,6-hexanedithiol, trimethylolpropanyl tris(3-mercaptopropionate), tetraethylene glycol bis(3-mercaptoproprionate), 1,4-butane diol bismercaptoacetate, asparagusic acid, lipoic acid, lipoamide, and combinations thereof. In a general procedure, allyl sucrose carbonate monomers are mixed with one or more multifunctional thiols in an appropriate solvent to produce a homogeneous resin. A radical initiator (1-10 wt %) is then added to the resin, which can be cast into a mold, allowing various geometries. Radical initiators can include, but are not limited to, 2,2-dimethoxy-2-phenylacetophenone, 2,2'-azobis(2-methylpropionitrile), potassium persulfate, benzoyl peroxide, 4,4'-azobis(4-cyanovaleric acid), and combinations thereof. Crosslinking/polymerization is initiated through exposure to UV irradiation, heat, or both to produce uniform bulk materials.

The properties of the bulk materials can be modulated and fine-tuned by varying the crosslinking conditions. For example, the number of allyl functionalities on the sucrose monomer, as well as the length and rigidity of the thiol comonomer, affect the crosslink density of the final material. The number of equivalents of thiol used compared to alkene also affect the crosslink density of the bulk material. The solvent used, which becomes trapped in the crosslinked network, also affects the properties of the bulk material. By varying these four factors, and others, materials with a range of moduli and degradation profiles can be generated.

Figures 6, 7:
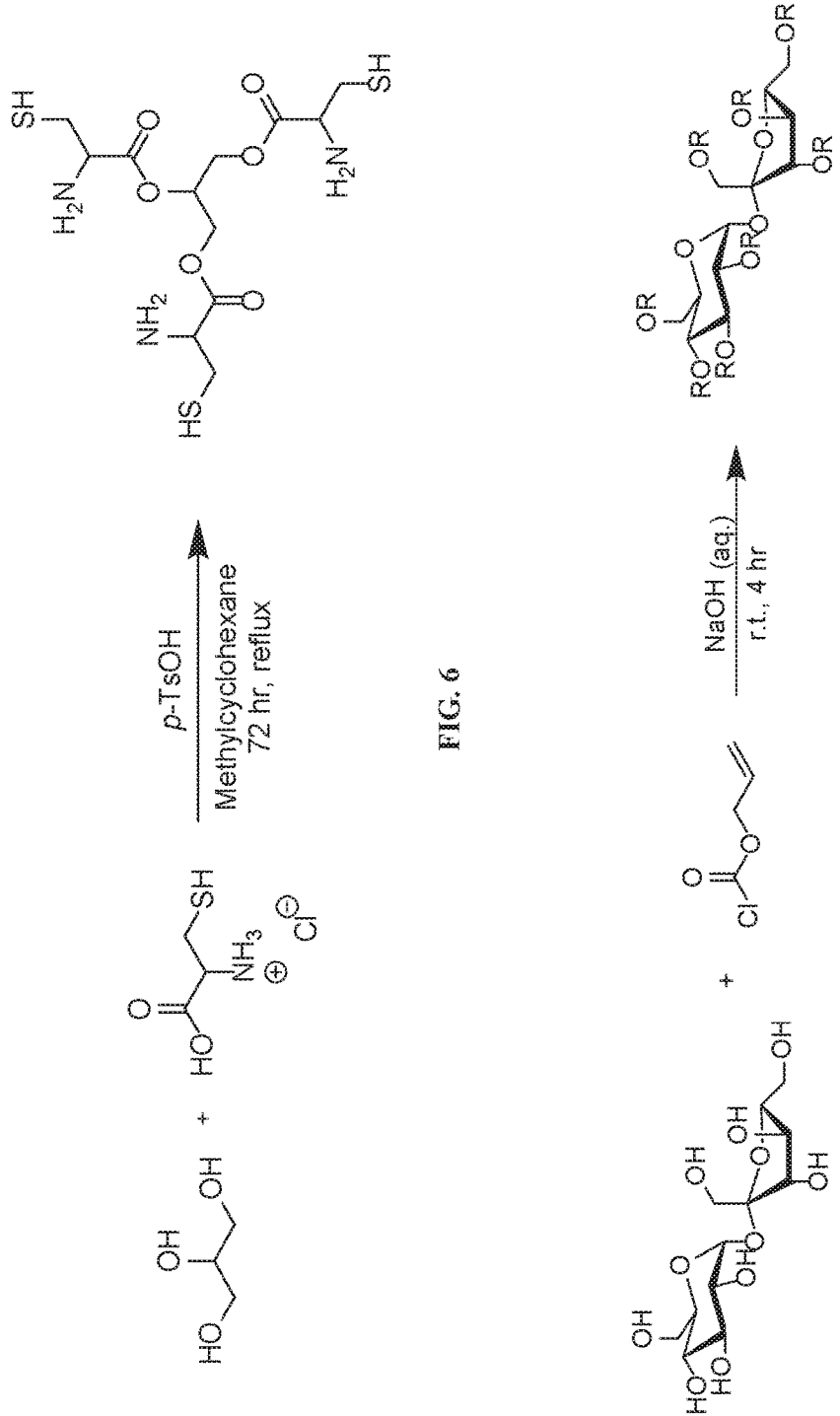
FIG. 6 is another reaction scheme for thiol preparation.
FIG. 7 is a reaction scheme for preparing allyl sucrose carbonate monomers.

A sucrose monomer network was prepared according to the reaction scheme of FIG. 7. Sucrose (50.094 g, 146.35 mmol) was dissolved in 50 mL of deionized water in a 250 mL two-neck round bottom flask fitted with two addition funnels. A solution of 19.32 g (483.0 mmol) NaOH in 47 mL of deionized water was added dropwise over 1 hour at 0° C. from one addition funnel while allyl chloroformate (46.7 mL, 439 mmol) was added simultaneously from the second addition funnel.

After addition was complete, the solution was stirred at room temperature for 3 hours before being neutralized by the addition of 0.5 M acetic acid. A majority of the water was removed on a high vacuum rotary evaporator, then the product was isolated by lyophilization (46 g, 4.65 average allyl groups per sucrose).

The allyl sucrose carbonate monomers were then crosslinked with various thiol comonomers. In a vial, allyl sucrose carbonate monomer (100 mg, 0.136 mmol) was dissolved in propylene glycol (200 μL) with heating and vortexing. The indicated thiol and chosen radical initiator were added and mixed into the resin by vortexing. Any additives can be incorporated at this step. The resin was loaded into a mold and cured by either exposure to UV light (365 nm) or heat (above 80° C.) for 1-10 minutes. After crosslinking, the resulting networks are stored in one of two ways: either immersed in solvent to preserve the solvent-swollen state, or placed under vacuum for 72 hours at 30° C. and then stored dry.

The thermal and mechanical properties of the resulting poly(thioether-co-carbonate) networks were characterized and the results are summarized in Table 5. Glass transition temperatures ($T_g$) of the dried samples were measured using differential scanning calorimetry ("DSC") by a Mettler-Toledo DSC822 (commercially available from Mettler-Toledo, Columbus, Ohio) with a heating rate of 10° C./min. The $T_g$ was taken as the midpoint of the inflection tangent upon the third heating cycle. Moduli values and $T_g$ values of the solvent swollen samples were measured on a TT-DMA dynamic mechanical analyzer from Triton Laboratories with a heating rate of 3° C./min. The $T_g$ was determined by the maximum of the tan(δ) peak.

TABLE 5

Thermal Transition Data and Moduli Exhibited by Thiol-Sucrose Networks.

| Solvent | Equivalents of Thiol | Solvent swollen/dried | $T_{d, onset}$ (° C.) | $T_g$ (° C.) | E' at 5° C. (MPa) | E' at 25° C. (MPa) |
|---|---|---|---|---|---|---|
| 1-Butanol | 0.5 | Swollen | 200 | 45 | 157 ± 10 | 101 ± 12 |
|  |  | Dried | 208 | 44 | 315 ± 23 | 180 ± 10 |
|  | 1 | Swollen | 226 | 36 | 99.6 ± 3.1 | 43.4 ± 2.8 |
|  |  | Dried | 242 | 33 | 202 ± 17 | 82.5 ± 5.2 |

TABLE 5-continued

Thermal Transition Data and Moduli Exhibited by Thiol-Sucrose Networks.

| Solvent | Equivalents of Thiol | Solvent swollen/dried | $T_{d,\,onset}$ (°C.) | $T_g$ (°C.) | E' at 5° C. (MPa) | E' at 25° C. (MPa) |
|---|---|---|---|---|---|---|
| | 2 | Swollen | 249 | 22 | 123 ± 20 | 13.1 ± 4.7 |
| | | Dried | 245 | 31 | 157 ± 4.6 | 26.2 ± 0.85 |
| 50/50 1-Butanol/ Propylene Glycol | 0.5 | Swollen | 219 | 32 | 53.8 ± 11 | 41.6 ± 2.0 |
| | | Dried | 212 | 55 | 42.4 ± 0.22 | 4.77 ± 1.3 |
| | 1 | Swollen | 258 | 26 | 48.8 ± 2.1 | 1.17 ± 0.52 |
| | | Dried | 223 | 35 | 47.7 ± 8.2 | 2.61 ± 0.12 |
| | 2 | Swollen | 267 | 25 | 105 ± 1.3 | 3.75 ± 3.0 |
| | | Dried | 245 | 25 | 90.5 ± 6.7 | 9.97 ± 1.9 |
| Propylene Glycol | 0.5 | Swollen | 215 | 32 | 22.1 ± 1.1 | 4.93 ± 0.49 |
| | | Dried | 216 | 39 | 60.9 ± 6.3 | 19.7 ± 0.94 |
| | 1 | Swollen | 258 | 30 | 71.5 ± 0.71 | 25.8 ± 0.78 |
| | | Dried | 235 | 37 | 69.6 ± 5.6 | 7.08 ± 2.6 |
| | 2 | Swollen | 265 | 18 | 62.3 ± 10 | 7.31 ± 0.16 |
| | | Dried | 251 | 17 | 18.4 ± 6.8 | 1.15 ± 0.21 |

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A hydrolytically-degradable device comprising a hydrolytically-degradable polycarbonate network, wherein the hydrolytically-degradable polycarbonate network comprises:
   a polyhydroxyl monomer that is a natural product, wherein at least one hydroxyl group of the polyhydroxyl monomer is modified with an allyl carbonate group, or any mixtures thereof;
   a crosslinking comonomer; and
   a functional additive.

2. The device of claim 1, wherein the polyhydroxyl monomer is a molecule comprising two or more hydroxyl groups.

3. The device of claim 1, wherein the polyhydroxyl monomer modified with an allyl carbonate group is an allyl glucopyranoside monomer.

4. The device of claim 1, wherein the polyhydroxyl monomer modified with an allyl carbonate group is an allyl sucrose monomer.

5. The device of claim 1, wherein the crosslinking comonomer is a thiol comonomer.

6. The device of claim 1, wherein the polycarbonate network has a glass transition temperature in the range of from −25° C. to 175° C.

7. The device of claim 1, wherein the polycarbonate network has a storage modulus in the range of from 0.1 MPa to 4000 MPa.

8. The device of claim 1, wherein the functional additive is selected from the group consisting of glitters, dyes, fragrances, flavorants, insect repellents, photoacid generators, pH sensitive moieties, plasticizers, tougheners, and any combination thereof.

9. A hydrolytically-degradable device comprising:
   a bulk material comprising:
   a polyhydroxyl monomer that is a natural product, wherein at least one hydroxyl group of the polyhydroxyl monomer is modified with an allyl carbonate group, or any mixtures thereof;
   a crosslinking comonomer; and
   a functional additive.

10. The device of claim 9, wherein the bulk material is a film or pellet.

11. The device of claim 9, wherein the polyhydroxyl monomer is a molecule comprising two or more hydroxyl groups.

12. The device of claim 9, wherein the polyhydroxyl monomer comprises an allyl glucopyranoside monomer.

13. The device of claim 9, wherein the polyhydroxyl monomer comprises an allyl sucrose monomer.

14. The device of claim 9, wherein the crosslinking comonomer is a thiol comonomer.

15. The device of claim 9, wherein the polycarbonate network has a glass transition temperature value in the range of from −25° C. to 75° C.

16. The device of claim 9, wherein the polycarbonate network has a storage modulus value in the range of from 0.1 MPa to 4000 MPa.

17. The device of claim 9, wherein the functional additive is selected from the group consisting of glitters, dyes, fragrances, flavorants, insect repellents, photoacid generators, sensitive moieties, plasticizers, tougheners, and any combination thereof.

18. A method comprising:
   providing a plurality of polyhydroxyl monomers that are natural products, wherein at least one hydroxyl group of each of the plurality of polyhydroxyl monomers is modified with an allyl carbonate group, or any mixtures thereof, a plurality of crosslinking monomers, and a functional additive;
   mixing the polyhydroxyl monomers, the plurality of crosslinking monomers, and the functional additive to form a resin;
   curing the resin to form a bulk material; and
   making a hydrolytically-degradable device that encounters an aqueous environment and degrades a set time thereafter.

19. The method of claim 18, wherein curing the resin to form a bulk material further comprises crosslinking the resin.

20. The method of claim 18, wherein curing the resin to form a bulk material further comprises irradiating the resin using UV light.

21. The method of claim 18, wherein curing the resin to form a bulk material further comprises heating the resin.

22. The method of claim 18, further comprising controlling at least one mechanical or physical property of the bulk material.

23. The method of claim 22, wherein at least one mechanical or physical property comprises a glass transition temperature value or a storage modulus value.

* * * * *